United States Patent [19]

Bichon et al.

[11] Patent Number: 4,892,733
[45] Date of Patent: Jan. 9, 1990

[54] BIODEGRADABLE SYNTHESIS POLYPEPTIDE AND ITS THERAPEUTIC USE

[75] Inventors: Daniel Bichon, Gaillard, France; Bernard Lamy, Carouge; William Borloz, Nyon, both of Switzerland

[73] Assignee: Imperial Chemical Industries PLC, London, England

[21] Appl. No.: 101,298

[22] PCT Filed: Dec. 15, 1986

[86] PCT No.: PCT/CH86/00177

§ 371 Date: Aug. 18, 1987

§ 102(e) Date: Aug. 18, 1987

[87] PCT Pub. No.: WO87/03891

PCT Pub. Date: Jul. 2, 1987

[30] Foreign Application Priority Data

Dec. 19, 1985 [CH] Switzerland ............... 5436/85

[51] Int. Cl.$^4$ ............................................. A61F 13/00
[52] U.S. Cl. ................................... 424/422; 424/1.1;
424/425; 424/426; 424/445; 424/450; 528/328;
530/300; 530/333; 623/11; 623/16; 623/66
[58] Field of Search ............... 424/426, 445, 450, 425,
424/1.1; 528/328; 530/300, 333; 623/1, 11, 16, 66

[56] References Cited

U.S. PATENT DOCUMENTS

| 4,046,722 | 9/1977 | Rowland | 530/382 X |
| 4,122,129 | 10/1978 | Casey et al. | 424/426 X |
| 4,172,128 | 10/1979 | Thiele et al. | 424/95 |
| 4,181,983 | 1/1980 | Kulkarni | 424/426 X |
| 4,322,398 | 3/1982 | Reiner et al. | 424/426 |
| 4,347,234 | 8/1982 | Wahlig et al. | 424/426 |
| 4,351,337 | 9/1982 | Sidman | 128/260 |
| 4,356,166 | 10/1982 | Peterson et al. | 424/19 |
| 4,363,797 | 12/1982 | Jacquet et al. | 528/322 X |
| 4,411,832 | 10/1983 | Cuatrecasas et al. | 530/395 X |
| 4,504,582 | 3/1985 | Swann | 424/78 X |
| 4,526,888 | 7/1985 | Williams et al. | 424/78 X |
| 4,578,217 | 3/1986 | Vnek et al. | 530/806 X |
| 4,638,045 | 1/1987 | Kohn et al. | 424/426 X |

FOREIGN PATENT DOCUMENTS

| 2424169 | 12/1974 | Fed. Rep. of Germany | 424/426 |
| 58-085814 | 5/1983 | Japan | 424/426 |

*Primary Examiner*—Thurman K. Page
*Attorney, Agent, or Firm*—Cushman, Darby & Cushman

[57] ABSTRACT

Derivatives of polyaspartic and/or polyglutamic acids whose side chains bear COOH groups capable to cyclize into anhydride. These polyacids and anhydrides can be used to manufacture medicines.

20 Claims, 1 Drawing Sheet

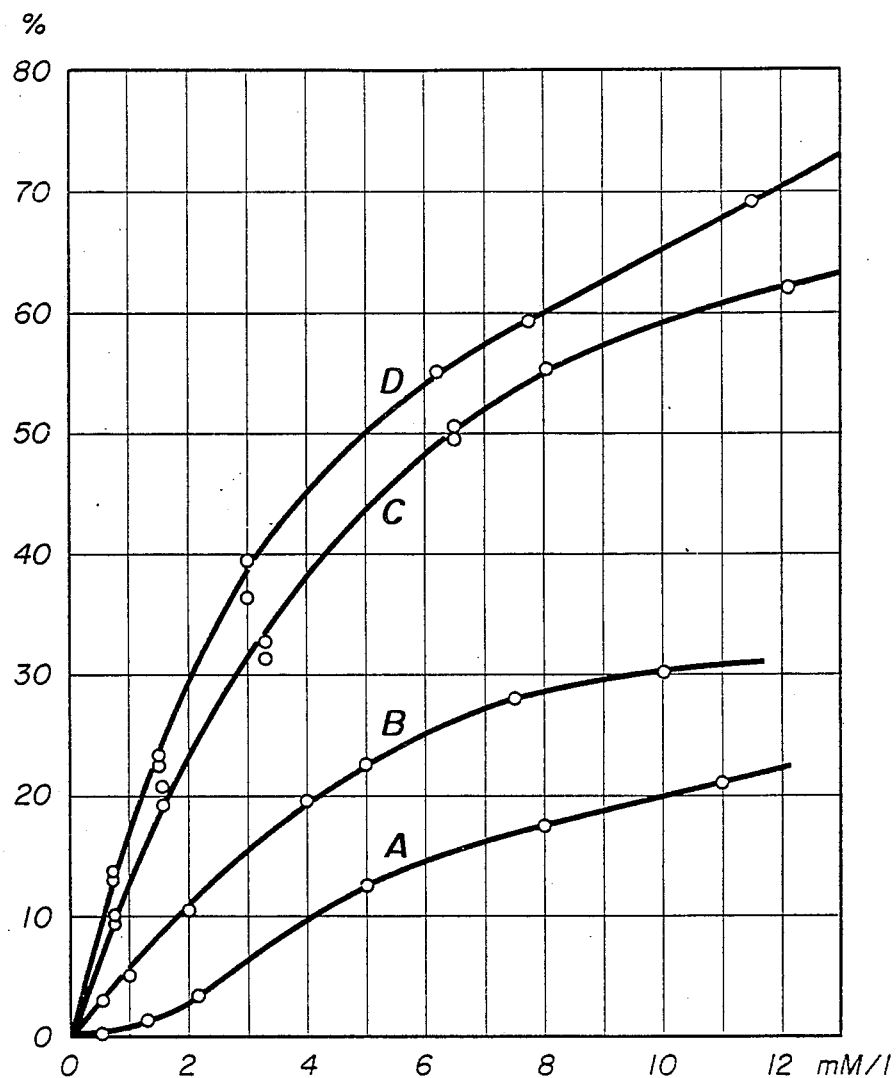

BIODEGRADABLE SYNTHESIS POLYPEPTIDE AND ITS THERAPEUTIC USE

The present invention has for an object a non-toxic, hydrosoluble, biodegradable polypeptide which can be used in biology and for various therapeutic applications, namely to be used as a drug carrier substrate, the drugs being thereafter progressively released in the organism as the biochemical degradation of the polymer progresses.

Non-toxic biodegradable polymers have been known for several years which can be used as drug reservoir and which make it possible to progressively and controllably release the drug in the organism as the degradation of the polymer carrier occurs. General information on this kind of products is to be found in "Fundamental Aspects of Biocompatibility" by D. F. WILLIAM, CRC Press (1981). See also U.S. Pat. No. 4,093,709.

Among these polymers, synthetic polypeptides (polyaminoacids) are more particularly cited whose structure is akin to that of proteins. These polypeptides are biocompatible and their degradation products (amino-acids) are resorbed by the organism. Thus, SIDMAN et al., (J. Membr. Sci. (1980), 7 (3), 277-91) disclose a glutamic acid -γ-ethyl-glutamate copolymer whose degradation rate is a function of the copolymer composition (molar ratio of esterified segments to non-esterified segments) which enables to store many products, for instance anti-cancer, anti-malarial drugs and the like. Such polymers can be used in the form of rods containing, in admixture, the desired drug or in the form of capsules containing the drug when the latter is not miscible with the polymer. However, alkyl polyglutamate and polyaspartate (straight esters of these polyacids) are degradable within a reasonable period (i.e. of a duration compatible with a pharmaceutical utilization) only when in partially hydrolyzed form (see for instance ASANO et al., J. Macromol. Sci. Chem. A21 (5) (1984), 561-582. For obtaining such partially esterified polymers, the polyglutamate or polyaspartates must be subjected to spare hydrolysis under conditions which are very difficult to reproduce. Moreover, very small differences of the extent of hydrolysis have a considerable influence on the rate of subsequent biodegradation which constitutes one further problem of using such polymers for the foregoing objectives.

Hence, despite the interest inherent to the aforementioned products, the search for a product of improved quality and, namely, with the following properties has been continued:

1. Excellent solubility in most current harmless solvents suitable for drugs, and even in water (effectively, the known polyaminoacid derivatives are generally only soluble in some special solvents (DMF, pyridine, $F_3CCOOH$) the use of which is inconvenient for pharmaceutical preparation).

2. Improved control of the degradation sequence. Effectively, the degradation rate of known synthetic polypeptides is tightly bound to their chemical structure, e.g. to the level of esterification. Thus, in a given case (see K. R. SIDMAN et al., PB 81-132,136 NTIS (1980), p.42), a variation of the level of esterification in the order of 10% changes the degradation rate from one to a hundred times (see also the foregoing SIDMAN reference), which raises problem of making reproducible samples.

DEFINITION OF THE INVENTION

The polymer of the invention (and its copolymers with other amino-acids) has made it possible to achieve these objectives, and still other ones which are not less important, as will be seen later. This polymer is an esterified polypeptide of formula:

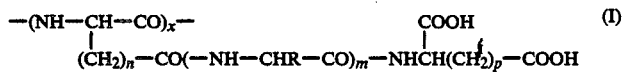

in which R is a rest of any amino-acid but, preferentially, is hydrogen (glycin), methyl (alanine) benzyl (phenylalanine), etc . . . However R can also designate amino-acid rests comporting OH, SH, $NH_2$ functions (which correspond to other aminoacids), as well as the COOH function (which corresponds to aspartic and glutamic acids), this carboxylic group can be free, partially esterified with a lower alkyl, or totally esterified.

In the foregoing formula I, n is equal to 1 or 2, m is equal to 0 or an integer from 1 to 4, p is equal to zero 1 or 2 and x has a value such that the molecular weight of the polymer be at least 5000 Dalton. The amide bond bridging the side carbon atom of the polyacid and the remaining sidechain is labelled as "isopeptide" bond.

It is seen from aforementioned formula I that in the case where m is equal to zero the polymer is a derivative of polyglutamine and, namely when p is equal to zero, of poly-γ-malonyglutamine. When p is equal to 1, we deal with poly-γ-succinylglutamine and when p is equal to 2, with asymmetric poly-γ-glutarylglutamine.

When m is different from zero, the molecule comprises a mono- or oligopeptide link inserted between the CO group of polyglutamine and the amino-substituted end group. The presence of one or more peptide groups in the side chain of the present polymer corresponds to the existence of one or more sites of hydrolysis attack leading to the degradation of the polymer into fragments resorbable by the organism in which the polymer is injected. Hence, by varying the number and the kind of aminoacids in the said link, one can accurately control the rate of degradation of the polymer in any given application. Among the preferred aminoacids for constituting these links, the followings can be recited: glycine, alanine, phenylalanine, esterified and non-esterified aspartic and glutanic acids, leucine, tyrosine, methionine and others.

The polymer of the invention can also exist in form of copolymer with other polyaminoacids. In this case, we have a copolymer of formula:

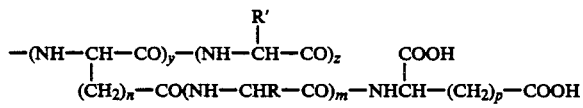

(II)

in which R' is any aminoacid rest, not-carboxylated or carboxylated: in this last case, the COOH groups can be free, partially esterified or totally esterified; the groups R' of the —(NH—CHR'—CO)— units can be identical or different in the copolymer chain, with y+z=x, the value of x being still appropriately selected for the copolymer to have an average molecular weight of at least 5000 Dalton. The definition of R' can therefore correspond to that of R. In general, it is preferred that R' represents the following groups: methyl (alanine), isopropyl (valine) isobutyl (leucine and isoleucine), benzyl (phenylalanine), etc. In essence, all other aminoacids are also possible although for obvious reasons it has not been possible to try them all. R' can also designate a glutanic or aspartic acid rest which is non-esterified or partially esterified by any alcohol, for instance MeOH or EtOH, i.e. for instance, —(CH$_2$)$_n$—COOH or (CH$_2$)$_n$—COOMe, n being 1 or 2. It should be noted that if R' defines a residue of free glutamic or aspartic acid, the polymer can be represented by formula I, although admittedly with a degree of substitution (amidation of the carboxyl group) less than 100%; naturally, this case can also be represented by formula II with R'=(CH$_2$)$_n$—COOH and y/(z+y) is equal to the degree of substitution.

It is also possible that the aminoacids be of the L-series or the D-series. The aminoacids of the L-series (or natural aminoacids) are more interesting as the polypeptides made therefrom are degradable by enzymes (proteases) in the human body, while the polypeptides containing the L-aminoacids are not biodegradable. One can take advantage of the difference and provide copolymers comprising D and L-aminoacids for having polymers whose degradation rate is modified according to a predetermined scheme.

Returning to more general consideration, it should be noted that the molar proportion, in copolymer II, of the other polyaminoacids which is free or partially esterified, also enables to control, to some significant degree, the copolymer degradation rate in function to the agents present in the organism at the target site where the copolymer/drug admixture is to be delivered (i.e. the organ in which the drug must be active). Thus, for instance if the copolymer is a copolymer of polyglutamine I and leucine, the relative molar proportion of both constituents is selected in function to the relative degradation rates, at the target site, of polyglutamine and polyleucine. In general, the ratio z/y can vary from 1 to 30, but both limits of this range can be extended if necessary.

Of course, in the case when group R' does not represent a group with a single definition in the copolymer chain, i.e. when for instance one of the R's represents a free aminoacid rest and another R' represents an esterified aminoacid rest, it is possible for simplicity to label the variants of R' by the letters R", R"', etc. Thus, the general formula of such a copolymer can be schematized as follows:

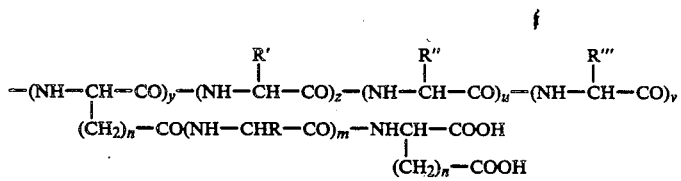

where the sum of the y, z, u, v, etc . . . is equal to x; the letters u, v, etc. can naturally be naught if the nature of the rest defined by R' is single. A typical case where the copolymer comprises different R' and R" is that when these groups represent glutamic and/or aspartic acid rests, some being esterefied and others not esterified; the shematic formula of a polymer of this kind (in the exemplification, the ester is methylated) is given as follows:

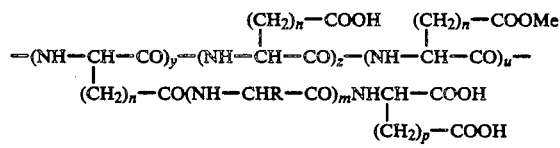

It is understood that, in regard to optical isomerism, the polymers of the invention can comprise elements with an L- or a D-configuration, or racemic mixtures, or polymers in which one of the configurations predominates. The biochemical properties of these various constructions are obviously not identical, the polymers in which the L-forms are dominant being more easily enzymatically degradable. One can therefore control the biodegradability, as mentioned before, by adjusting the relative proportion of both forms in the polymer.

Polymers I and copolymers II are water-soluble (even at acid pH) in contrast to polyglutamic acid (unless the COOH groups are esterified and soluble generally in one or more solvents of the group including dimethylformamide, trifluoroacetic acid, dichloroacetic acid, trifluoroethanol.

The biodegradation of polymer I can be schematized as follows:

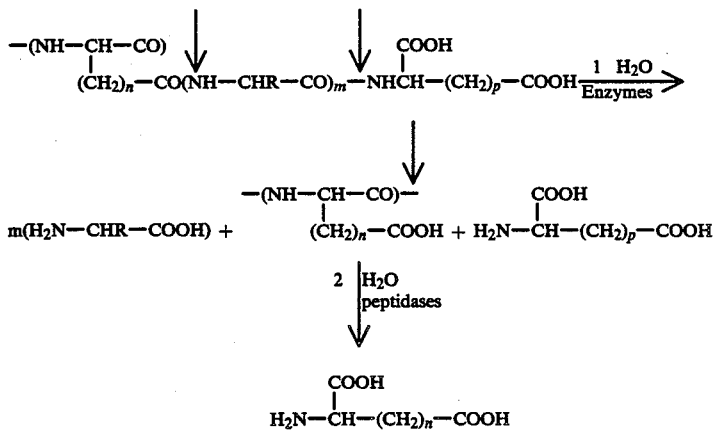

Reaction (2) is subsequent to reaction (1) and, as a consequence, the faster the hydrolysis of the side chain, higher the rate of the biodegradation of the polymer.

In the above reaction scheme, little arrows indicate the bonds broken by enzymatic hydrolysis (for instance due to the γ-glutamyltranspeptidase present in the organism); thus, by appropriately selecting the aminoacids forming this side-chain, one may adjust the degradation rate in function to the hydrolysis conditions at the polymer delivery site and therefore control the release of the drugs contained in the polymer. The enzymatic hydrolysis properties of graft peptides are well illustrated in the following reference: J. KOPECER et al., "Enzymatically Degradable Bonds in Synthetic Polymers" in Controlled Drug Delivery, Vol. I, basic concepts, CRC Press, p. 81 (1983).

Several routes are available to prepare polymer I and copolymer II. Thus, for instance in the case where m=o (absence of bridging links between the polyacid carbonyl group and the substituted nitrogen group of glutamine), one may react polyaminoacid IV, or the desired corresponding co-polyaminoacid with an alkyl-aminomalonate, -aspartate or -glutamate III (for instance, alkyl is tert-butyl) in the presence of dicyclohexylcarbodiimide (DDC) which provides the ester corresponding to polyacid I or II, the latter being thereafter hydrolyzed by usual means. The reaction scheme of this route of preparation is given herebelow. In this scheme the letter Y represents an ester group, for instance methyl, butyl, benzyl, etc.

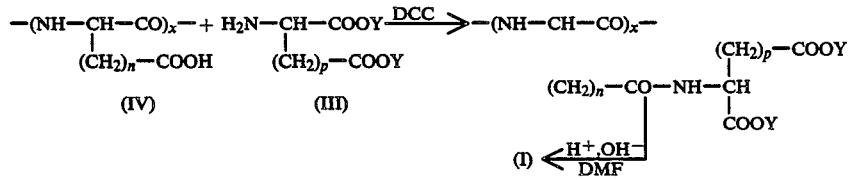

In the case when an intermediate bridging link is inserted in the side-chain (m=0), one may, according to an embodiment, constitute first this side-chain form the diester III by progressively lenking thereto by usual means one or more aminoacids, then one may connect this chain to the polyaminoacid as in the above scheme.

A schematic example of this kind-of-processus is given below in which the diester III derives from amino-malonic acid and the intermediate links derive, successively, from phenylalanine and glycine. It is noted that for the addition of these intermediate links, the amino-function of the aminoacids is protected by a benzoxycarbonyl group (Z) and a reagent, hydroxybenzotriazole (HOBt) is used, jointly with dicyclohexylcarbodiimide, to prevent racemization.

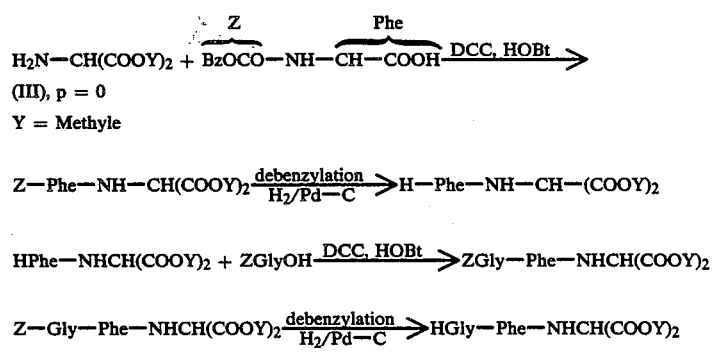

-continued

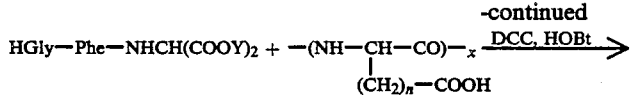

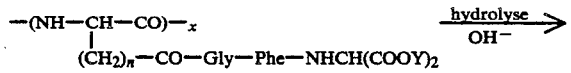

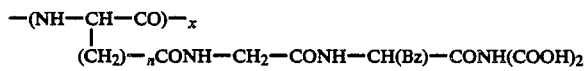

(I) $m = 2; R_1 = H; R_2 = Bz; p = 0$

According to a second embodiment, one can proceed in the reverse direction, i.e. in the foregoing exemplified case react the starting polyacid with glycine (esterified beforehand) in the presence of DCC, eliminate the protective ester group, react the polymer thus obtained with a phenylalanine ester, and so on until the final chain is obtained. The stages of this embodiment being obvious per se for somebody skilled in the art, it is not necessary to provide more details here.

Naturally, the techniques used for the preparation of the polymer I are also suitable in the case of copolymers II, the difference relating only to the choice of the starting polyacid, i.e. to replacing polyacid IV by a corresponding co-polyacid, for instance

The polyaminoacid IV or the copolyaminoacid V which are used as starting materials for the preparation of polymer I or copolymer II is easily obtainable by usual means which comprise esterifying with a lower alcohol. The side carboxyl group of an acid of formula

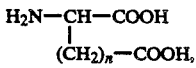

The conversion of the ester in a corresponding N-carboxyanhydride (NCA) with phosgene in a dioxane or THF medium, polymerizing the NCA into an esterified polyaminoacid and hydrolyzing the protective ester group in alkaline medium or with trifluoroacetic acid. Such methods are known per se (see for instance Encyclopedia of Polymer Science & Technology; N-carboxyanhydride, Vol. II, page 837). When it is desired to obtain a copolymer where R' represents a partially esterified carboxyl group (R'=—(CH$_2$)$_n$—COOH and R"=—(CH$_2$)$_n$—COOAlk) care is taken that hydrolysis of the protective ester group be only partial. Thus, for instance, the starting material (V) to be used in a case is an acid/ester copolymer H$_2$NCH[(CH$_2$)$_n$—COOH—]—COOH/H$_2$NCH[(CH$_2$)$_n$—COOAlk]—COOH.

Because of the presence along the chain of two carboxylic groups, polymers I and II can bind some carboxylic ions, e.g. Ca$^{+2}$, more strongly than monocarboxalic acids. A property of this kind exists for some natural polypeptides present in the organism, e.g. prothrombin, blood factor Xa, osteocalcin of bones and gristle; these compounds are provided with γ-carboxyglutamic rests (Gla) capable of bonding Ca$^{+2}$ (see J. P. BURNIER et al., Molecular and Cellular Biology 39 (1981), 191-199). In particular, osteocalcin has a strong affinity for hydroxyapatite and, although its physiological action is still poorly known, it probably has an important action in the control of bone growth.

Regarding prothrombin, this compound is provided with ten Gla rests in its molecule which allow prothrombin to bind, in the presence of calcium, to the phospholipids which constitute cellular membranes. In these conditions, prothrombin has the property of being connected, in the presence of factor Xa, into thrombin which induces blood clotting by catalyzing the transformation of fibrinogen into fibrin.

Yet, some compounds of the invention, namely poly-(γ-malonylglutamic) acid

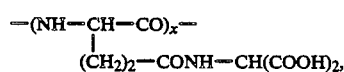

have a structure very similar with that of Gla rests:

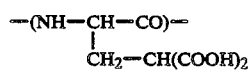

and analogous properties.

Hence, they can be used for manufacturing bone and cartilage prosthesis which are entirely biocompatible and biodegradable without toxic residue formation. One may achieve such prosthesis by moulding mixtures of powdered hydroxyapatite with, as binders, polymers of the invention, alone or as admixtures with other biodegradable polymers. For such an object, it is preferred to use polymers I or II in which p=0. These prosthesis are very rigid mechanically but they slowly resorb as the regeneration of the consolidated bone progresses. Thus, an usual eventual operation to remove the prosthesis after healing can be avoided.

The present carboxylic polypeptides can be used to provide cyclic anhydrides, when p is equal to 1 or 2, for example by treating poyacids I or II with carbodiimide such as DDC, as shown below:

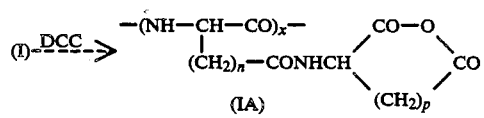

This transformation results in the formation of polymers which are insoluble in water but soluble in many usual organic solvents, e.g. acetone, methyl-ethyl ketone, THF, dioxane, ethylacetate, monoglyme and the like which makes it possible to easily convert them into beads, rods, fibers, filaments, microcapsule, etc. by extrusion, moulding, evaporation and so on. By hydrolysis, the polymers IA, and also their homologs IIA identically obtained from copolymers II revert to the polyacids I and II.

Polymers IA and copolymers IIA are biodegradable and biocompatible when used for slowly and controllably releasing drugs, for instance in the form of thin films prepared by spreading a solution of the polymer and a drug on a substrate and thereafter evaporating to dryness the solvents of the solution. These techniques are disclosed in "Controlled Release of Macromolecules from Polymers" by R. LANGER et al., Biomedical Polymers, Ed. GOLDBERG & NAKAJIMA, Academic Press (1980). When the film has dried, the drug can stay therein in the dissolved state or in the form of a particle suspension.

Polymer IA and copolymer IIA can be used for drug storage by various means. For instance, the present polymer IA and copolymer IIA can be used to manufacture microcapsules containing a drug. These microcapsules have a polymer membrane filled with an aqueous or oily solution in which the drug stays dissolved or as a suspension. One can also manufacture microspheres, i.e. solid particles or beads with the drug being stored in the form of a dispersion or solid solution within the polymer matrix. One can also manufacture microporous products called microsponges. In general, all the techniques involving the manufacture of slow release drugs, i.e. items with the property of releasing the drug over an extended period as the degradation of the carrier progresses, can be implemented with the present polymers. A description of these techniques can be found in the following references: "Biodegradable and Delivery Systems for Contraception", E. S. E. HAFEZ, MTP Press Ltd. (1980); "Controlled Release Technologies=Methods, Theory and Applications", Vol. 1 and 11, A. F. KYDONIEUS, CRC Press (1980); and "Microencapsulation-New Techniques and Applications" by Tamotsu KONDO, Techno Inc. (1979) Japan. The solubility of the present polymers in many solvents miscible or not miscible with water is an advantage for their application according to the techniques disclosed in these references. It is also possible to prepare threads from these polymers by extruding a solution thereof through a spinneret and by precipitating the thread, either by evaporation, or with a non-solvent bath, according to the usual spinning techniques. Filaments prepared by these methods can be knitted, tied or woven to provide sutures, ligature or tubular structures usable as artifical arteries, veins, tubes or temporary operating internal organs. The polymers of the invention can also be used directly or as admixtures with a plasticizer to make films or Surgical prosthesis to be used for instance for mending broken bones, as stitches, needles, screws, reinforcing plates, plugs, etc . . . ; these materials can be made by solution moulding, thermoforming or machining solid polymer blocks. These prosthesis are resorbable and progressively eliminated by the body, therefore it is no longer necessary to undertake a new operation to remove the reinforcing and consolidation material.

The polymers and copolymers of the invention are also usable for the preparation of biodegradable surgical dressings. These dressings are constituted by one or more layers obtained in succession from solution of the polymers in a solvent coated on a substrate and solidified by evaporation or drying.

It is possible for instance to achieve such dressings by coating a substrate with the solution (these solution may or not contain one or more drugs, a germicide for example) under sterile conditions, removing the solvent by heat or under vacuum, then peeling the film off the substrate and possibly drying it again before use (or packaging the film under sterile conditions if it is not to be used immediately).

Wound dressings of this sort are made of one or more successive layers of polymers deposited successively on a substrate as layers of solutions in a water-compatible solvent, these layers being solidified by water extraction of the solvent. One such extraction can be performed by contacting with water, e.g. by washing or dipping.

One may achieve such dressings by coating a substrate with the solutions (these solutions may or not contain one or more drugs, a germicide for example) under sterile conditions, by treating the substrate with water then by removing the unsolubilized film therefrom and by possible drying it before use (or packaging the film under sterile conditions if it must not be used immediately). The inherent advantage of polypeptides IA and IIA over the polyalkylglutamate or-aspartate of the prior art is provided by the unstability character of the anhydride rings which enables to effect the dissolution/biodegradation of the polymer in its hydrophobic anhydride form.

The anhydride compounds IA and IIA are also useful as drug vectors for covalently binding drugs with a function which can react with the cycle, for instance an amino-function (of an enzyme, of a protein, of a polypeptide), as shown below where M defines a drug molecule to be linked to the present polymer:

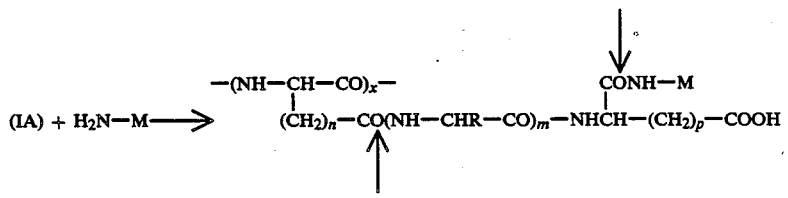

Once the polymer has been modified by binding with drug M, it can be handled as previously disclosed and given in the same manner so as to act at the target place in the organism. In some cases the pharmacological effect is inherent to the modified polymer itself but, most often, the drug becomes active when it is freed from its substrate, for instance by hydrolysis. In the foregoing scheme, the arrows point to the bonds which may break by hydrolysis.

Regarding the state of the art in this field, one notes that grafting pharmaceutically active molecules on soluble macromolecular substrates is known; in particular, many references exist on the grafting techniques used and on the advantages of the products obtained, the latter being generally definies as "pharmacologically active polymers". The following books teaching these subjects can be mentioned:

Polymers in Medicine, Advances Polym. Science No. 57, Springer Ed. (1984).

Polymeric Drugs, Ed. DONAMURA & VOGI, Academic Press (1978).

Phamacologically active polyers of the vinyl type (acrylic) have been disclosed with a major defect of not being biodegradable. In contrast, pharmacologically active substances have been grafted on degradable polysaccharides (Dextran for instance; see HASHIDA et al., Drug Metab. Dispos. 12 (1984), 492-499).

Polyminoacids have also been used as substrates for drugs, namely in cancerotherapy. Thus, poly-L-lysine has been used as a substrate for anticancer drugs (SHEN and RYSER, Molecul. Pharmacol. 16 (1979), 614-622). Polyaspartic acid has also been used to link daunorubicine. Moreover, the use of polyglutamic acid as a carrier for norethindrone (contraceptive) has been reported (ZUPON et al., J. Pharm. Science 72 (1983), 1323-1326), as well as for an antitumor target drug by conjugation with an antibody (ROWLAND et al., Nature (London) 255 (1975), 487-488; WILCHEK, Makromol. Chem. Suppl. 2 (1979), 207-214). More recently, new antitumor polymers based on mitomycine C (ROOS et al., Intl. J. of Pharmaceutics 22 (1984), 75-87) have been synthesized from polyglutamic or polyaspartic acid and polylysine. Furthermore, KATO et al., J. Med. Che. 27 (1984), 1602-1607, have disclosed a method for coupling daunomycine to an antibody by linking to polyglutamic acid Also, adriamycine (anticancer drug) has been linked to polyglutamic acid (Van HEESWIJK et al., J. of Controlled Release 1 (1985), 301).

Moreover, copolymers of maleic anhydride and another vinyl monomer have often been used in medical applications. On one hand, these polymers have an intrinsic pharmacologic activity after hydrolysis (this is namely the case for divinylethermaleic anhydride DIVEMA which acts as macrophase activator). On the other hand, they can be used in anhydride form as drug carriers, namely by the reaction of the anhydride function with a R-OH or R-NH$_2$ group of an active compound similarly with the anhydrides derived from the polyacids of the invention (HIRANO et al., Makromol. Chem. 180 (1979), 1125. A drawback of these polymers of the prior art is their lack of biodegradability and they accumulate in the lysosomes which later leads to an ailment called "Macromolecular Syndrome" or Thesaurosis (W. C. HUEPER, Arch. Path. 28 (1939), 510.

The polymers of the invention as well as the corresponding anhydrides can be used to form soluble macromolecules carrying an active factor which can be thereafter slowly released. It is noted that, as compared with the known examples of the aforementioned prior art, they have the following advantages:

Their use is simple (intermediate coupling agents are useless)

Their solubility in water is good even with a high binding level because of the formation when linking the drug (coupling) of a —COOH (hydrophilic) group.

As mentioned previously, polymers I and II have a considerable interest because of their complexing capacity (chelatant) toward some metal ions, e.g. $Ca^{+2}$, this property resulting from the presence of dicarboxylic side groups. Dicarboxylic groups —$CH(COOH)_2$ which can chelate calcium exist in $\gamma$-carboxyglutamic acid to be found in certain human proteins (see J. P. BURNIER et al., "Gamma carboxyglutamic acid", Molecular and Cellular Biology 39 (1981), 191-199, namely in bones and cartilage.

This property of binding calcium, which is particularly significant in the case of the aspartic derivative (I, p=1) renders the compounds of the invention particularly useful for manufacturing bone and cartilage prosthesis which are fully biocompatible and resorbable. A prosthesis of this kind can be achieved by moulding a mixture of powdered hydroxyapatite $Ca_{10}(PO4)_6(OH)_2$ and a binder constituted by the polymer or copolymer of the invention in which p is preferably zero. One such prosthesis is very rigid mechanically when used in an application, but it slowly resorbs as the natural regeneration of the reinforced member progresses which allows to suppress the usual eventual removal operation after healing.

The following example illustrate the invention in detail.

BRIEF DESCRIPTION OF THE DRAWING

The annexed drawing is a graph for illustrating the complexation ability toward calcium of the polymers according to the invention.

General Synthetic Methods

The polymers and copolymers of the invention are synthesised as follows: one first prepares conventionally poly-L-glutamic acid or poly-L-aspartic acid by the N-carboxyanhydride method (see for instance patent application CH-5021/84).

Generally, it is preferred for polyglutamic acid to start from the alkyl-$\gamma$-benzyl glutamate N-carboxyanhydride($\gamma$-benzylglutamate-NCA) which provides high molecular weights polymers. The poly-$\gamma$-benzylglutamate obtained is thereafter debenzylated with HBr in benzene to give poly-L-glutamic acid.

One prepares polyaspartic acid similarly by the polymerization of $\beta$-benzylaspartate-NCA and subsequent debenzylation of the polyacid-ester. The molecular weights are generally lower with polyaspartate than with polyglutamate.

EXAMPLE 1

Synthesis of poly-($\gamma$-L-aspartyl-glutamine) and its anhydride.

One uses as the starting polymer a compound poly-$(Glu(OMe))_{20}$—$Glu(OH)_{80})$, i.e. a polyacid corresponding to formula V in which $R' = (CH_2)$—COOMe, $y = 0,8$ and $z = 0,2$ (x being of course one). This polymer prepared by incomplete hydrolysis of poly-(Glu(OMe) in aqueous trifluoroacetic acid (this polymer therefore comprise in its backbone 20% of methyl glutamate units).

One dissolves 3,8 g of poly(Glu(OMe) $_{20}$Glu(OH)$_{80}$) in 30 ml of dimethylformamide (DMF) which corresponds to 23.04 mmole of —COOH groups. Twenty five mmole of hydroxybenzotriazole with 8% H$_2$O, i.e. 3.67 g, are added, then 25 mmole of di-t-butyl-L-aspartate. HCL, i.e. 7.04 g, 6 ml of tributylamine (TBA) and 5.16 g of dicyclohexylcarbodiimide (DCC). After 20 hrs agitation at ambient temperature, the mixture is centrifugated. The bottom residue (dicyclohexylurea) is washed with CHCl$_3$ (50 ml) and the extract is added to the upper liquid. One further dilutes with 100 ml of CHCl$_3$ and one successively washes this phase with H$_2$O (3×100 ml), NaHCO$_3$ 1N (2×100 ml), H$_2$O (100 ml), 1% HCl (3×100 Ml) and H$_2$O (2×100 ml). The organic phase is dried over Na$_2$SO$_4$ and concentrated to 40 ml. A hexane/ether mixture is added until the mixture becomes milky and the latter is poured over 550 ml of a mixture of hexane and petroleum-ether (35°-45°), which induces precipitation. The precipitate is dissolved in 20 ml of CHCl$_3$ and 100 ml of ether are added; the solution is filtered, hexane is added to the filtrate and the precipitated product is dried under vacuum. 5.72 g of polymer are obtained of which most has the formula:

The 5,72 g of polymer are dissolved in 20 ml of trifluoroacetic acid (TFA), and 40 ml of CHCl$_3$ are added, then a few ml of acetone until turbidity appears. The solution is poured over 400 ml of acetone under violent agitation. The fine precipitate is taken in 200 ml of acetone+200 ml of ether, then it is drained and dried. The polymer IIA, 3.68 g (yield 90%), corresponds to the following formula (theory):

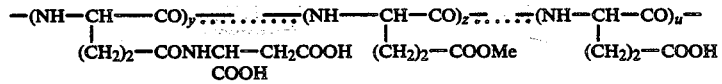

A sample of polymer is hydrolyzed 12 hrs in 6N HCl at 120° C.

Analysis of the aminoacids composition of the solution indicates the presence of 3 moles of aspartic acid for 4 moles of glutamic acid which provides the following values of molecular indice: y=0.75; z=0.2; u=0.05. Furthermore, the NMR spectrum of the polymer in TFA solution corresponds to the proposed structure. The product obtained is very hygroscopic and should be stored in the dessicator.

One dissolves 0,927 g of the above poly (Glu(OMe) Glu(OH)Glu(Asp)) in 10 ml of DMF and 3 mmole of DCC are added. After 20 hrs of agitation, the mixture is filtered and 30 ml of ether are added to the filtrate. The liquid is then poured into 350 ml of ether and 200 ml of petroleum-ether are added which results in the separation of a solid. The precipitate is centrifugated and the solid is dried to provide 0.73 g of a polymer insoluble in water but soluble in CHCl$_3$. The IR spectrum of this polymer confirms the presence of anhydride functions ($\delta$=1800 cm$^{-1}$) and its formula is consequently as follows:

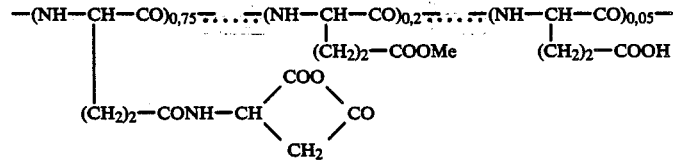

EXAMPLE 2

Synthesis of poly ($\gamma$-L-glutamyl-glutamine) and its anhydride.

One dissolves 2.5 g of poly-L-glutamic acid (0.0192 moles COOH) in 50 ml DMF and there is added successively, 2.85 g hydroxybenzotriazole, 3.63 g tributylamine, 0.7 g of dibenzyl glutamate hydrochloride and 3.95 g of dicyclohexylcarbodiimide (DCC). The mixture is agitated for 24 hrs at ambient temperature. The dicyclohexylurea formed is filtered out and the filtrate is evaporated (40° C./1 Torr). The precipitate is dissolved in chloroform (50 ml) and washed with, successively, NaHCO$_3$ 0.1N, H$_2$O, 1% HCl and saturated brine (100 ml). After each washing, centrifugation is effected to separate the organic and aqueous phases. The organic phase is finally dried over MgSO$_4$, filtered and precipitated by the addition of an excess of ether. The polymer is redissolved in MeOH (20 ml), acetic acid (30 ml) and water (5 ml) are added; two g of palladium on activated carbon are added and hydrogen is bubbled for 15 h in the suspension. After filtering off the activated carbon, the solution is dialyzed for 3 days in distilled water, then it is freeze-dried which provides 3.5 g of poly ($\gamma$-L-glutamyl-glutamine).

The polymer may be stored in its dicarboxylic acid form, or it can be cyclized as follows:

One dissolves 1.44 g of the polymer in 200 ml of DMF and one adds thereto 2.3 g of DCC. The mixture is agitated for 24 hrs; then at 70° C. the dicyclotexylurea (DCU) is filtered out and ether is added which causes the polymer to precipitate. An IR spectrum of a thin film of this polymer resulting from coating a glass plate with a CHCl$_3$ solution of polymer shows the presence of anhdride (1 peak at 1830cm$^{-1}$).

By working as in previous example 1, but replacing the polyglutamic acid by the corresponding polyaspartic acid, there is obtained the corresponding poly ($\gamma$-L-aspartyl-L-aspartamine). This compound can by cyclized into its corresponding anhydride by the aforementioned means.

Identically, by using as the starting polyacid a 50/50 copolymer of glutamic acid and leucine, one first obtains a copolymer of formula

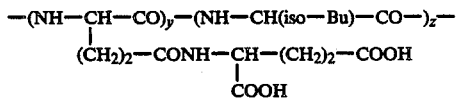

where y=z=0.5 with x=1, then the corresponding anhydride by the aforementioned means.

EXAMPLE 3

The binding of amino-compounds on polyglutamine-anhydrides.

The following reactions were carried out with the polyacids of the invention in the form of anhydrides and some aminoacids: Aqueous or DMF aminoacid solution were added dropwise to DMF solution of polypeptides. The mixture was left for 14 hrs under agitation, after which the polymer obtained was connected to a salt with NaHCO$_3$N/10 and a 24 hrs dialysis in H$_2$O was carried out followed by freeze-drying. Samples of the obtained products were analyzed (after hydrolyzing in 6N HCl) for the extent of binding of the aminoacids. The results are gathered in the table below: It is noted from the results that the extent of binding depends partly on the solubility of the starting products in the reaction medium:

| Polypeptide anhydride | Amino Compound | Reaction Medium | Binding Level % |
|---|---|---|---|
| poly(Glu-glutamine)-anhydride | glycine methyl-ester | DMF good solubility | 75% |
| " | Alanine | DMF + H$_2$O | 20% |
| poly(Asp(anh)glu-tamine | Glycine | DMF + H$_2$O mean solubility) | 50% |

In general, the solvent or mixture of solvents for the reaction medium should be selected or preferentially promote the reaction of the —NH$_2$ of the substance to be bound as compared with the hydrolysis of the anhydride ring.

EXAMPLE 4

Poly (γ-2-(dicarboxy-1,3-propyl)-glutamine).

We deal here with the polyglutamide of 2-amino malonic acid whose chemical name, according to IUPAC nomenclature is poly{imino-[1-oxo-2(1',3'-dicarboxy-2'-iminocarbonylethylene)-ethylene]}.

One dissolves 5 g of polyglutamic acid (PGA) in 100 ml of DMF; one adds thereto, successively, 7.16 g of thributylamine, 7.10 g of dimethylaminomalonate hydrochloride and 5.23 g of HOBt. The mixture is cooled to 0° C. and there is added 7.97 g of DCC dissolved in 20 ml of DMF. After 24 hrs, the mixture is filtered and the polymer is precipitated by the addition of water. The solid is redissolved in acetone and reprecipitated with water. Then it is again redissolved in acetone and reprecipitated with water. Then it is again redissolved in CHCl$_3$ and the solution is dried over MgSO4. The solution is filtered on a fritted glass funnel and ether is added to precipitate. There is obtained 5.8 g of esterified polymer with the following formula:

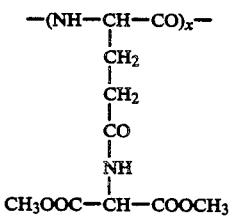

The NMR spectrum of the polymer as the solution in trifluoroacetic acid corresponds to the above formula (δ=3.15 ppm, OCH$_3$). The polymer (3 g) is added to 30 ml of KOH N/10 in MeOH. Then 25 ml of H$_2$O are added. The polymer dissolves progressively. After 17 hrs, the pH is brought back to 7 and the solution is dialyzed for one day in water, then in HCl 1%. The residue is freeze dried and there is obtained 2.4 g of polymer of formula

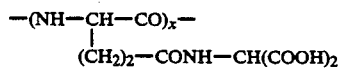

The proportion of aminoacids in a sample is measured after total hydrolysis thereof in 6N HCl (24 hrs). The analysis concerns the determination of glycine which forms, during hydrolysis, by decarboxylation of the aminomalonic rest. The analysis indicates that the yield of binding of malonyalmido is 85%.

EXAMPLE 5

Poly-(γ-aspartyl-glycine-glutamine-anhydride)

The dipeptide of following formula is prepared first

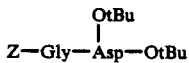
Z—Gly—Asp—OtBu by a conventional dicyclohexylcarbodiimide coupling of Z-Gly(OH) and H$_2$N-Asp(Ot.Bu)$_2$. This dipeptide is then catalytically debenzylated by H$_2$/Pd to give HGly-Asp(Ot.Bu)$_2$. This peptide is crystallized in the form of the dibenzylsulfimide salt (HN(SO$_2$-Bz)$_2$) in ether. It is thereafter coupled with polyglutamic acid as in the previous examples. The DCU formed is filtered off, the polymer is precipitated in NaHCO$_3$ 0.1N, it is washed with H$_2$O and then dissolved in dioxane saturated with HCl (4N). After 20 min, the polymer precipitates. The mixture is evaporated to dryness and the product is dissolved in carbonate buffer, pH 7. The solution is filtered to eliminate the insoluble component and it is dialyzed in H$_2$O for 24 hrs, then in 1% HCl for 24 hrs. Freeze-drying the solution provides a polymer with the following formula:

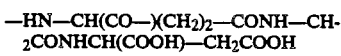

This polymer is taken in DMF and, to the solution, there is added 1.5 equiv. of DCC. After reacting for 24 hrs, the DCU is filtered off, the DMF is evaporated and the polymer is redissolved in a minimum of chloroform. The solution is filtered to remove the last trace of DCU, the polymer is precipitated by a 50/50 mixture of ether and petroleum-ether and the solid is dried under vacuum.

An Ir spectrum is measured of a film of this polymer obtained from a solution in trifluoroacetic acid and shows the presence of anhydride groups (λ=1830cm$^{-1}$).

Analysis of the aminoacids provided by a total hydrolysis of the polymer shows that the grafting level is 78%.

EXAMPLE 6

The object of this example is to stress the complexing power toward calcium ions of various polymers according to the invention.

In a series of dialysis membrane envelops (guts) were introduced 1 ml portions of aqueous solution containing radioactive Ca$^{+2}$, 100 μl of $^{45}$Ca 10$^{-3}$M and variable quantities of various polymers according to the invention (as well as of a control). The polymers under investigation were: polyglutamic acid (A, control); poly-(malonyl-glutamine) B; poly-(aspartylglutamine) C; poly-(glutaryl-glutamine) D.

The envelops were placed in 7 ml of phosphate buffer, pH 7.5, and the dialysis was allowed to proceed up to equilibrium (24 hrs); then by means of a scintillation counter, the calcium concentrations were measured in the buffer, both outside of the membrane and inside thereof in the dialyzed solution. The ratio (%) of the calcium bound to polymer relative to total Calcium was then determined. Results are collected in the annexed graph in function (abcissa) to the quantity of polymer expressed in mMoles/l of the carboxyl bearing groups and show that polyglutamic has only a very limited capacity to bind calcium compared to the dicarboxylic peptides of the invention.

EXAMPLE 7

This example will show that the poly-(γ-malonylglutamine) derivative binds to lipid surfaces in the presence of $CA^{+2}$ like prothrombin (see for instance S. P. BAJAJ et al., Journal of Biol. Chemistry, 250 (6) (1975), 2150-2156).

The operations were carried out as follows:

A liposome suspension was first prepared by dissolving 250 mg of lecithin in 36 ml of $CHCl_3$, adding 10 ml of buffer (20 mM Tris, HCl +'mMol NaCl, pH 7.5) and ultrasonication of the mixture at 50° C. After evaporating the $CHCl_3$, 30 ml of buffer were added, the total volume was adjusted to 40 ml and centrifugation was carried out for ½ hr at 60000 rpm. The bottom was taken back in 41.6 ml of buffer to provide a liposome suspension containing 6 mg/ml.

Then, aqueous solution, 10 mM of Ca ions containing each 2 mg/ml of liposomes and increasing quantities (from 0,025 to 1 mg/ml of poly-(γ-malonylglutamine) labelled with $^{14}C$, were placed in a serie of test-tubes. The technique used for labelling poly-(γ-malonylglutamine) was to react it with $^{14}C$ radioactive methyl glycinate in the presence of 2-ethoxy-1-ethoxycarbonyl-1,2-dihydroquinoleine (EEDQ) in order to effect substitution of about 1% of the malonyl rests by glycinate and achieve a specific activity for the polymer of 37,000 dpm/mg (disintegration/min).

After 30 min, the liposomes were centrifugated out and the extent of radioactivity was measured in the supernatant liquor, this value defining the percent of poly-(γ-malonylglutamine) unbound by liposomes. The results are collected in the following table:

| No tube | Polymer (mg/ml) | Ca$^{++}$ (mM) | Liposomes (mg/ml) | Unbound % polymer |
|---|---|---|---|---|
| 1 | 1 | 10 | 0 | 95,7 |
| 2 | 0,025 | 0 | 2 | 92,0 |
| 3 | 0,025 | 10 | 2 | 5,0 |
| 4 | 0,05 | 10 | 2 | 21,8 |
| 5 | 0,1 | 10 | 2 | 48,2 |
| 6 | 0,25 | 10 | 2 | 76,3 |
| 7 | 0,5 | 10 | 2 | 84,4 |
| 8 | 0,75 | 10 | 2 | 90,0 |
| 9 | 1 | 10 | 2 | 92,2 |

These results show that 1 mg of liposomes binds 0,5 mg of poly-(γ-malonylglutamine) in the presence of calcium. One also sees (trial No. 2) that in absence of $Ca^{+2}$, the polymer does not bind the liposomes. Thus, under the aforementioned conditions, the polymers behavior is analogous to the natural behavior of a blood protein.

EXAMPLE 8

The following polymers, poly-(γ-glutamylglutamine), poly-(γ-aspartylglutamine), poly-(γ-malonylglutamine) were dissolved in isotonic NaCl solution at pH 7.4 (0.0m phosphate) to provide a concentration of 100 mg/ml.

Solutions were injected i.p. to white mice (25-30 g) up to 2000 mg/kg (5 tests per dose). After a 4 weeks observation period no lethal effect on the experimental animals was noted, up to a dose of 2000 mg/kg.

We claim:

1. Hydrosoluble, biodegradable, carboxylated polypeptide derived from polyaspartic and/or polyglutamic acids, of formula

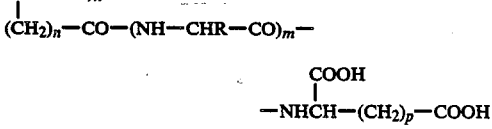

or its copolymers with other aminoacids, of formula

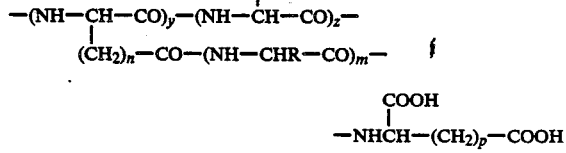

in which:

R and R' are side chains of aminoacids, and R' is the same or different than R;

m is an integer from 0 to 5;

p is 0, 1 or 2;

n is 1 or 2;

x is selected so that the molecular weight of the polypeptide is at least 5000 Dalton; and x=y+z with the ratio of y/z being in the range of about 1 to about 30.03.

2. Polypeptide according to claim 1 wherein R is selected from the group consisting of methyl, hydrogen, isobutyl, isopropyl and benzyl.

3. Polypeptide according to claim 1 wherein said intermediate link is selected from the group of aminoacids consisting of glycine, alanine, valine, leucine, isoleucine, phenylalanine, tyrosine, serine, cysteine, methionine, lysine and arginine.

4. Polypeptide according to claim 1 wherein the backbone of compound I is selected from the group consisting of polyglutamic and polyaspartic acids and that the backbone of compound II is selected from the group consisting of copolymers of aspartic acids and glutamic acids with one or more aminoacids selected from the group consisting of alanine, leucine, valine and phenylalaline.

5. Polypeptide according to claim 1 wherein copolymer II is a copolymer of polyglutamine or polyaspartamine with comonomers selected from the group consisting of glutamic acid, lower alkyl glutamates, aspartic acid, and lower alkyl aspartates.

6. Polypeptide according to claim 1, wherein the carboxylic acid groups are in the form of salts with alkali or earth-alkali cations or with primary, secondary or tertiary amines, or they are in the form of cyclic anhydrides.

7. A method of use of polypeptides I and copolymers II according to claim 1 as slow-release drug carrier in bodies, the drug being progressively released at the target place consecutive to the biodegradation of the carrier polymer.

8. The method according to claim 7 wherein said polymer and drug are mixed together homogeneously and the mixture is formed into a pharmaceutically acceptable form.

9. The method according to claim 8 wherein the polymer is mixed with a plasticizer, adding a drug thereto, then thermoforming the thermoplastic product thus obtained into granules, rods, capsules or other particles suitable for being given to patients.

10. The method of use of polymers I and copolymers II according to claim 1, to manufacture implants and biodegradable prosthesis to be used in surgery.

11. The method of use according to claim 7, wherein polymers I and copolymers II are put into reaction in their form of cyclic anhydrides with a substance capable of reacting with anhydride, whereby they will covalently bind to said polymers.

12. The method of use according to claim 11 wherein said covalent bond is biodegradable at the target site of the polymer in an organism.

13. The method of use of claim 11 wherein said substance reacts with the anhydride through an amino, amido, hydroxy or thiohydroxy function.

14. The method of use according to claim 10 for the preparation of biodegradable bone implants or prosthesis wherein said prosthesis are constituted from hydroxyapatite bound with said polymers I or copolymers II.

15. The method of use of polymer I and copolymers II as antiviral and antitumor drugs.

16. Method for the preparation of polymers I and copolymers according to claim 1, where $m=o$ wherein a polyacid of formula $-(NH-CH((CH_2)_n-COOH)-CO)_x$ (IV), or a corresponding co-polyacid of formula $-(NH-CH((CH_2)_n-COOH)-CO-_y$ $-(NH-CHR'-CO)_z$ (V) with an aminoacid ester of formula $H_2N-CH((CH_2)_p-COOY)-COOY$ (III), where Y represents an alkyl of esterification, in the presence of dicyclohexylcarbodiimide, so as to obtain polymers I and copolymers II in esterified form, then the ester-polymers are subjected to dealkylation by hydrolysis or catalytic hydrogenolysis so that said ester-polymers are converted to free carboxylic acids.

17. Method according to claim 16 where $m \neq 0$, wherein there is used, instead of ester III, a diester of formula $H_2N-CHR-CO-(NH-CHR-CO)_m-NH-CH((CH_2)_p-COOY)-COOY$.

18. Method according to claim 17 wherein a diester of formula VI is obtained by successive coupling steps of diester III, in the presence of dicyclohexylcarbodiimide, with, successively, aminoacids whose $NH_2$ is temporarily blocked by a protective group and this protective group is removed by dehydrogenation after each coupling steps.

19. The polypeptide of claim 1 wherein some or all of the groups R and R' carry a free COOH group, a partially esterified group or a totally esterified COOH group.

20. The method of claim 18 wherein the protective group is benzyloxycarbonyl.

* * * * *

UNITED STATES PATENT AND TRADEMARK OFFICE
CERTIFICATE OF CORRECTION

PATENT NO. : 4,892,733

DATED : January 9, 1990

INVENTOR(S) : BICHON ET AL

It is certified that error appears in the above-identified patent and that said Letters Patent is hereby corrected as shown below:

On the title page:

Correct the name of the Assignee from "Imperial Chemical Industries PLC, London, England" to -- Battelle Memorial Institute, Geneva, Switzerland --.

Signed and Sealed this

Ninth Day of October, 1990

Attest:

HARRY F. MANBECK, JR.

*Attesting Officer*  *Commissioner of Patents and Trademarks*